United States Patent
Swindle

(10) Patent No.: US 8,143,498 B2
(45) Date of Patent: Mar. 27, 2012

(54) COTTON VARIETY FM 1740B2F

(75) Inventor: Michael Swindle, Greenville, MS (US)

(73) Assignees: Bayer CropScience Ag, Monheim (DE); Cotton Seed International Proprietary Limited, New South Wales (AU)

( * ) Notice: Subject to any disclaimer, the term of this patent is extended or adjusted under 35 U.S.C. 154(b) by 91 days.

(21) Appl. No.: 12/463,222

(22) Filed: May 8, 2009

(65) Prior Publication Data

US 2009/0282576 A1 Nov. 12, 2009

Related U.S. Application Data

(60) Provisional application No. 61/126,893, filed on May 8, 2008, provisional application No. 61/195,542, filed on Oct. 8, 2008.

(51) Int. Cl.
*A01H 1/00* (2006.01)
*A01H 4/00* (2006.01)
*A01H 5/00* (2006.01)
*A01H 5/10* (2006.01)
*C12N 15/82* (2006.01)

(52) U.S. Cl. ........ 800/314; 800/260; 800/263; 800/264; 800/265; 800/278; 800/279; 800/300; 800/302; 435/421; 435/427

(58) Field of Classification Search ............ 800/260, 800/263, 264, 265, 278, 279, 314, 300, 302; 435/410, 421, 427
See application file for complete search history.

(56) References Cited

U.S. PATENT DOCUMENTS

| | | | |
|---|---|---|---|
| 6,008,438 A | 12/1999 | Keim | |
| 6,740,488 B2 | 5/2004 | Rangwala et al. | |
| 6,818,807 B2 | 11/2004 | Trolinder et al. | |
| 7,057,098 B2 * | 6/2006 | Holland et al. | 800/314 |
| 2004/0148666 A1 | 7/2004 | Rangwala et al. | |
| 2009/0049564 A1 | 2/2009 | Burdett | |

FOREIGN PATENT DOCUMENTS

EP 0 270 355 6/1988
WO WO 00/71733 11/2000

OTHER PUBLICATIONS

Briggs, F.N. and Knowles, P.F., "Introduction to Plant Breeding," Chapters 11, 13 & 18, Reinhold Publishing Corporation, (1967).
Sakhanoko, H.F. et al., "Induction of Somatic Embryogenesis and Plant Regeneration in Select Georgia and Pee Dee Cotton Lines." Crop Science 44: 2199-2205 (2004).
Stam, P. "Marker-assisted Introgression: Speed at Any Cost?" Proceedings of the Eucarpia Meeting on Leafy Vegetable Genetics and Breeding, Noordwijkerhout, The Netherlands, Mar. 19-21, 2003. Eds. Th.J.L. van Hintum, A. Lebeda, D. Pink, J.W. Schut. p. 117-124 (2003).

* cited by examiner

*Primary Examiner* — David T Fox
*Assistant Examiner* — Keith Robinson
(74) *Attorney, Agent, or Firm* — Hunton & Williams

(57) ABSTRACT

The cotton variety FM 1740B2F is disclosed. The invention relates to seeds, plants, plant cells, plant tissue, harvested products and cotton lint as well as to hybrid cotton plants and seeds obtained by repeatedly crossing plants of variety FM 1740B2F with other plants. The invention also relates to plants and varieties produced by the method of essential derivation from plants of FM 1740B2F and to plants of FM 1740B2F reproduced by vegetative methods, including but not limited to tissue culture of regenerable cells or tissue from FM 1740B2F.

27 Claims, No Drawings

COTTON VARIETY FM 1740B2F

CROSS-REFERENCE TO RELATED APPLICATIONS

This application claims the benefit of U.S. Provisional Application No. 61/126,893, filed May 8, 2008, and U.S. Provisional Application No. 61/195,542, filed Oct. 8, 2008, the disclosures of each of which are herein incorporated by reference in their entirety.

BACKGROUND OF THE INVENTION (i) Field of the Invention

This invention relates to the field of plant breeding. More particularly, the invention relates to a variety of cotton designated as FM 1740B2F, its essentially derived varieties and the hybrid varieties obtained by crossing FM 1740B2F as a parent line with plants of other varieties or parent lines.

(ii) Description of Related Art

Cotton is an important, fiber producing crop. Due to the importance of cotton to the textile industry, cotton breeders are increasingly seeking to obtain healthy, good yielding crops of excellent quality.

Cotton is commonly reproduced by self-pollination and fertilization. This type of sexual reproduction facilitates the preservation of plant and variety characteristics during breeding and seed production. The preservation of these characteristics are often important to plant breeders for producing cotton plants having desired traits. Other methods of producing cotton plants having desired traits are also used and include methods such as genetic transformation via *Agrobacterium* infection or direct transfer by microparticle bombardment. Examples of such methods are disclosed, for example, in U.S. Pub. No. 20090049564, incorporated by reference herein in its entirety.

Due to the environment, the complexity of the structure of genes and location of a gene in the genome, among other factors, it is difficult to predict the phenotypic expression of a particular genotype. In addition, a plant breeder may only apply his skills on the phenotype and not, or in a very limited way, on the level of the genotype. As a result, a particular plant breeder cannot breed the same variety twice using the same parents and the same methodology. Thus, a newly bred variety is an unexpected result of the breeding process. Indeed, each variety contains a unique combination of characteristics.

By carefully choosing the breeding parents, the breeding and selection methods, the testing layout and testing locations, the breeder may breed a particular variety type. In addition, a new variety may be tested in special comparative trials with other existing varieties in order to determine whether the new variety meets the required expectations.

SUMMARY OF THE INVENTION

The invention relates to seeds, plants, plant cells, parts of plants, cotton lint or fiber, and cotton textiles of cotton variety FM 1740B2F as well as to hybrid cotton plants and seeds obtained by repeatedly crossing plants of FM 1740B2F with other cotton plants. The invention encompasses plants and plant varieties produced by the method of derivation or essential derivation from plants of FM 1740B2F and to plants of FM 1740B2F reproduced by vegetative methods, including but not limited to regeneration of embryogenic cells or tissue of FM 1740B2F. The invention also encompasses methods of producing cotton seeds that comprise crossing plants of cotton variety FM 1740B2F either with itself or with a second, distinct cotton plant.

DETAILED DESCRIPTION OF THE PREFERRED EMBODIMENTS

The invention has been obtained by a general breeding process comprising the steps outlined below. For reference, see chapter 11, "Breeding Self-Pollinated Crops by Hybridization and Pedigree Selection," in Briggs and Knowles (1967).

Parent plants, which have been selected for good agronomic and fiber quality traits are manually crossed in different combinations. The resulting F1 (Filial generation 1) plants are self-fertilized and the resulting F2 generation plants, which show a large variability on account of optimal gene segregation, are planted in a selection field.

These F2 plants are observed during the growing season for health, growth vigor, plant type, plant structure, leaf type, stand ability, flowering, maturity, seed yield, boll type, boll distribution, boll size, fiber yield and fiber quality. Plants are then selected. The selected plants are harvested and the bolls analyzed for fiber characteristics and the seed cleaned and stored. This procedure is repeated in the following growing seasons, whereby the selection and testing units increase from individual plants in the F2, to multiple plant containing 'lines' (descending from one mother plant) in the F5 and the number of units decrease from approximately 2500 plants in the F2 to 20 lines in the F5 by selecting about 10-20% of the units in each selection cycle.

The increased size of the units, whereby more seed per unit is available, allows the selection and testing in replicated trials on more than one location with a different environment and a more extensive and accurate analyzing of the fiber quality.

The lines or candidate varieties become genotypically more homozygous and phenotypically more homogeneous by selecting similar plant types within a line and by discarding the so called off-types from the very variable F2 generation on to the final F7 or F8 generation.

Depending on the intermediate results the plant breeder may decide to vary the procedure described above, such as by accelerating the process by testing a particular line earlier or retesting a line another year. He may also select plants for further crossing with existing parent plants or with other plants resulting from the current selection procedure.

By the method of recurrent backcrossing, as described by Briggs and Knowles, supra, in chapter 13, "The Backcross Method of Breeding", the breeder may introduce a specific trait or traits into an existing valuable line or variety, while otherwise preserving the unique combination of characteristics of this line or variety. In this crossing method, the valuable parent is recurrently used to cross it at least two or three times with each resulting backcross F1, followed by selection of the recurrent parent plant type, until the phenotype of the resulting F1 is similar or almost identical to the phenotype of the recurrent parent with the addition of the expression of the desired trait or traits.

This method of recurrent backcrossing eventually results in an essentially derived variety, which is predominantly derived from the recurrent parent or initial variety. This method can therefore also be used to get as close as possible to the genetic composition of an existing successful variety. Thus, compared to the recurrent parent the essentially derived variety retains a distinctive trait, which can be any phenotypic trait, with the intention to profit from the qualities of that successful initial variety.

Depending on the number of backcrosses and the efficacy of the selection of the recurrent parent plant type and genotype, which can be supported by the use of molecular markers as described by P. Stam (2003), the genetic conformity with the initial variety of the resulting essentially derived variety may vary between 90% and 100%.

Other than recurrent backcrossing, as described herein, such essentially derived variety may also be obtained by the selection from an initial variety of an induced or natural occurring mutant plant, or of an occurring variant (off-type) plant, or of a somaclonal variant plant, or by genetic transformation of regenerable plant tissue or embryogenic cell cultures of the said initial variety by methods well known to those skilled in the art, such as *Agrobacterium*-mediated transformation as described by Sakhanokho et al, (2004), Reynaerts et al. (2000), Umbeck et al. (1988) and others. Examples of transgenic events transformed in this way are "LLCotton25," USDA-APHIS petition 02-042-01p, "Cot 102," USDA-APHIS petition 03-155-01p, and "281-24-236," USDA-APHIS petition 03-036-01p combined with "3006-210-23," USDA-APHIS petition 03-036-02p. Information regarding these and other transgenic events referred to herein may be found at the U.S. Department of Agriculture's (USDA) Animal and Plant Health Inspection Service (APHIS) website. An "Event" is defined as a (artificial) genetic locus that, as a result of genetic engineering, carries a foreign DNA comprising at least one copy of the gene(s) of interest. Other methods of genetic transformation are well known in the art such as microprojectile bombardment. See, e.g., U.S. Publication No. 20090049564, which is incorporated by reference herein in its entirety.

The plants selected or transformed retain the unique combination of the characteristics of FM 1740B2F, except for the characteristics (e.g., one, two, three, four or five characteristics) changed by the selection of the mutant or variant plant or by the addition of a desired trait via genetic transformation. Therefore, the product of essential derivation (i.e., an essentially derived variety), has the phenotypic characteristics of the initial variety, except for the characteristics, that change as a result of the act of derivation. Plants of the essentially derived variety can be used to repeat the process of essential derivation. The result of this process is also a variety essentially derived from said initial variety.

In one embodiment, FM 1740B2F progeny plants are produced by crossing plants of FM 1740B2F with other, different or distinct cotton plants, and further selfing or crossing these progeny plants with other, distinct plants and subsequent selection of derived progeny plants. The process of crossing FM 1740B2F derived progeny plants with itself or other distinct cotton plants and the subsequent selection in the resulting progenies can be repeated up to 7 or 8 times in order to produce FM 1740B2F derived cotton plants.

FM 1740B2F has been obtained by introducing the Event MON 88913 (APHIS petition 04-086-01p) via a cross between a donor plant containing this Event and the BCSI cotton line "E0088", followed by two subsequent backcrosses of the F1 plants resulting from these crosses, that express the characteristics of E0088 combined with the Event as described above, with plants of E0088. The resulting line is being designated as "E0088F BC2F1". At the same time the two Bollgard Events MON 531 (Crylac, APHIS petition nr 94-308-01p) and MON 15985 (Cry2ab, APHIS petition nr 00-342-01p) were introgressed in line E0088 by the same method of recurrent backcrossing, resulting in line "E0088B2 BC2F1". In order to combine or 'stack' the three Events the lines "E0088F BC2F1" and "E0088B2 BC2F1" were crossed resulting in the line "E0088B2F BC3F1".

Following two selfing generations in the glasshouse, seed from each plant were planted in the field as individual rows. Rows were selected in the field on the basis of the Bollgard Events expression, resistance to glyphosate herbicide, leaf type, leaf hair, disease resistance, lint % and fiber quality. Following progeny row testing for yield, disease resistance and fiber quality, selected sister-lines proceeded to replicated, multiple site trials. These multiple site trials were conducted in mid-south and south east regions of the cotton belt. At the same time small seed increases were initiated for all lines.

Sister-lines from the mid-south and south east trials were selected based on performance in these regions and bulked. This bulk constitutes the finished variety FM 1740B2F.

Provided herein as embodiments of the invention are seeds, plants, plant cells and parts of plants of the cotton variety FM 1740B2F. Representative seeds of this variety have been deposited under rule 37CFR1.809, under ATCC Accession No. PTA-12373. Plants produced by growing such seeds are provided herein as embodiments of the invention. Also provided herein are pollen or ovules of these plants, as well as a cell or tissue culture of regenerable cells from such plants. In another embodiment, the invention provides for a cotton plant regenerated from such cell or tissue culture, wherein the regenerated plant has the morphological and physiological characteristics of cotton cultivar FM 1740B2F, as described herein (e.g., Table 1), when grown in the same environmental conditions. In yet another embodiment, the invention provides methods of testing for a plant having the morphological and physiological characteristics of cotton cultivar FM 1740B2F. In one embodiment, the testing for a plant having the morphological and physiological characteristics of cotton cultivar FM 1740B2F is performed in the same field, under the same conditions and in the presence of plants of FM 1740B2F, e.g., plants grown from the seed deposited under ATCC Accession No. PTA-12373. In another embodiment, the characteristics to be tested for are those described herein (e.g., Table 1).

In another embodiment, the present invention provides regenerable cells for use in tissue culture of cotton cultivar FM 1740B2F. The tissue culture will preferably be capable of regenerating plants having the physiological and morphological characteristics of the cotton cultivar FM 1740B2F, and of regenerating plants having substantially the same genotype as the cotton plant of the present invention. Preferably, the regenerable cells in such tissue cultures will be from embryos, protoplasts, meristematic cells, callus, pollen, leaves, anthers, pistils, roots, root tips, flowers, seeds, pods or stems. Still further, the present invention provides cotton plants regenerated from the tissue cultures of the invention.

Yet another aspect of the current invention is a cotton plant of the cotton variety FM 1740B2F comprising at least a first transgene, wherein the cotton plant is otherwise capable of expressing all the physiological and morphological characteristics of the cotton variety FM 1740B2F. In particular embodiments of the invention, a plant is provided that comprises a single locus conversion. A single locus conversion may comprise a transgenic gene which has been introduced by genetic transformation into the cotton variety FM 1740B2F or a progenitor thereof. A transgenic or non-transgenic single locus conversion can also be introduced by backcrossing, as is well known in the art. In certain embodiments of the invention, the single locus conversion may comprise a dominant or recessive allele. The locus conversion may confer potentially any desired trait upon the plant as described herein.

Single locus conversions may be implemented by backcrossing wherein essentially all of the desired morphological and physiological characteristics of a variety are recovered in addition to the characteristics conferred by the single locus transferred into the variety via the backcrossing technique. A single locus may comprise one gene, or in the case of transgenic plants, one or more transgenes integrated into the host genome at a single site (locus).

In a particular aspect, the invention provides for a method of introducing a single locus conversion into cotton cultivar FM 1740B2F comprising: (a) crossing the FM 1740B2F plants, grown from seed deposited under ATCC Accession No. PTA-12373, with plants of another cotton line that comprise a desired single locus to produce F1 progeny plants; (b) selecting F1 progeny plants that have the desired single locus to produce selected F1 progeny plants; (c) crossing the selected F1 progeny plants with the FM 1740B2F plants to produce first backcross progeny plants; (d) selecting for first backcross progeny plants that have the desired single locus and the physiological and morphological characteristics of cotton cultivar FM 1740B2F as described herein (e.g., Table 1), when grown in the same environmental conditions, to produce selected first backcross progeny plants; and (e) repeating steps (c) and (d) one or more times (e.g. one, two, three, four, etc. times) in succession to produce selected third or higher backcross progeny plants that comprise the desired single locus and all of the physiological and morphological characteristics of cotton cultivar FM 1740B2F as described herein (e.g., Table 1), when grown in the same environmental conditions. Plants produced by this method have all of the physiological and morphological characteristics of FM 1740B2F, except for the characteristics derived from the desired trait.

Another embodiment of the invention provides for a method of producing an essentially derived plant of cotton variety FM 1740B2F comprising introducing a transgene conferring the desired trait into the plant, resulting in a plant with the desired trait and all of the physiological and morphological characteristics of cotton variety FM 1740B2F when grown in the same environmental conditions. In another embodiment, the invention provides for a method of producing an essentially derived cotton plant from FM 1740B2F comprising genetically transforming a desired trait in regenerable cell or tissue culture from a plant produced by the invention, resulting in an essentially derived cotton plant that retains the expression of the phenotypic characteristics of cotton variety FM 1740B2F, except for the characteristics changed by the introduction of the desired trait.

Desired traits described herein include modified cotton fiber characteristics, herbicide resistance, insect or pest resistance, disease resistance, including bacterial or fungal disease resistance, male sterility, modified carbohydrate metabolism and modified fatty acid metabolism. Such traits and genes conferring such traits are known in the art. See, e.g., US 20090049564, incorporated by reference herein in its entirety.

The invention also provides for methods wherein the desired trait is herbicide tolerance and the tolerance is linked to a herbicide such as glyphosate, gluphosinate, sulfonylurea, dicamba, phenoxy proprionic acid, cyclohexanedione, triazine, benzonitrile, bromoxynil or imidazalinone. The invention also provides for methods wherein the herbicide tolerance is an expression of the Event "LLCotton25" and the insect resistance is an expression of the Event "281-24-236", Event "3006-210-23" or a combination thereof, or Event "Cot 102".

In one embodiment, the desired trait is insect resistance conferred by a transgene encoding a Bacillus thuringiensis (Bt) endotoxin, a derivative thereof, or a synthetic polypeptide modeled thereon.

Also included herein is a method of producing cotton seed, comprising the steps of using the plant grown from seed of cotton variety FM 1740B2F, of which a representative seed sample will be deposited under ATCC Accession No. PTA-12373, as a recurrent parent in crosses with other cotton plants different from FM 1740B2F, and harvesting the resultant cotton seed.

Another embodiment of this invention relates to seeds, plants, plant cells and parts of plants of cotton varieties that are essentially derived from FM 1740B2F, being essentially the same as this invention by expressing the unique combination of characteristics of FM 1740B2F, including the herbicide and insect resistance of FM 1740B2F, except for the characteristics (e.g., one, two, three, four, or five characteristics) being different from the characteristics of FM 1740B2F as a result of the act of derivation.

Another embodiment of this invention is the reproduction of plants of FM 1740B2F by the method of tissue culture from any regenerable plant tissue obtained from plants of this invention. Plants reproduced by this method express the specific combination of characteristics of this invention and fall within its scope. During one of the steps of the reproduction process via tissue culture, somaclonal variant plants may occur. These plants fall within the scope of this invention as being essentially derived from this invention.

Another embodiment of the invention provides for a method of producing an inbred cotton plant derived from the cotton variety FM 1740B2F comprising: (a) preparing a progeny plant derived from cotton variety FM 1740B2F, a representative sample of seed of said variety having been deposited under ATCC Accession No. PTA-12373, by crossing cotton variety FM 1740B2F with a cotton plant of a second variety; (b) crossing the progeny plant with itself or a second plant to produce a seed of a progeny plant of a subsequent generation; (c) growing a progeny plant of a subsequent generation from said seed and crossing the progeny plant of a subsequent generation with itself or a second plant; and (d) repeating steps (b) and (c) for an additional 3-10 generations with sufficient inbreeding to produce an inbred cotton plant derived from the cotton variety FM 1740B2F.

Another embodiment of this invention is the production of a hybrid variety, comprising repeatedly crossing plants of FM 1740B2F with plants of a different variety or varieties or with plants of a non-released line or lines. In practice, three different types of hybrid varieties may be produced (see, e.g., Chapter 18, "Hybrid Varieties" in Briggs and Knowles, supra): the "single cross hybrid" produced by two different lines, the "three way hybrid", produced by three different lines such that first the single hybrid is produced by using two out of the three lines followed by crossing this single hybrid with the third line, and the "four way hybrid" produced by four different lines such that first two single hybrids are produced using the lines two by two, followed by crossing the two single hybrids so produced. Each single, three way or four way hybrid variety so produced and using FM 1740B2F as one of the parent lines contains an essential contribution of FM 1740B2F to the resulting hybrid variety and falls within the scope of this invention.

The invention also provides for cotton lint or fiber produced by the plants of the invention, plants reproduced from the invention, and plants essentially derived from the invention. The final textile produced from the unique fiber of FM 1740B2F also falls within the scope of this invention. The invention also provides for a method of producing a commodity plant product (e.g., lint, cotton seed oil) comprising obtaining a plant of the invention or a part thereof, and producing said commodity plant product therefrom.

The entire disclosure of each document cited herein (e.g., US patent publications, non-patent literature, etc.) is hereby incorporated by reference.

Example 1

Breeding Cotton Variety FM 1740B2F

Seeds were obtained from the bulked sister lines finally selected in the process of breeding the new variety "FM 1740B2F".

Seeds of the variety FM 1740B2F, of which a representative sample will be deposited, were planted, together with seeds of cotton variety FM 958 as reference variety, in field trials at two locations, as discussed hereunder.

Location 1:
1. BCSI Research Station, Leland, Miss. 2007. Conditions: Planting date May 15, trial conducted under irrigation with conventional management. Trial was designed to measure distinguishing characters, yield and fiber: 14 entry trial, random complete block design with 6 replications, (the plot for each rep, consisted of two 14 m rows). For distinguishing characters: measurements were taken from 10 plants, of each plot.

Location 2:
2. Azlin Farms, Leland, Miss. 2007. Conditions: Planting date May 15, trial conducted under irrigation with conventional management. Trial was designed to measure distinguishing characters, yield and fiber: 14 entry trial, random complete block design with 6 replications, (the plot for each rep, consisted of two 14 m rows). For distinguishing characters: measurements were taken from 10 plants, of each plot.

Analysis of variance procedures were used to obtain least significant difference at the 5% level, using Agrobase software.

Table 1 reflects the average expression of the characteristics of FM 1740B2F on these locations in 2007. This expression can be different on other locations and/or in other years. The sample that will be deposited represents the variety and this sample can be analyzed for the expression of its phenotypic characteristics at any time and at any location.

FM 1740B2F is most similar and closely resembles DP 555BG/RR, but can be distinguished from its comparator variety DP 555BG/RR by the following: FM 1740B2F contains a second Bt gene (MON 15985), while DP 555BG/RR does not. In addition, the herbicide event in FM 1740B2F (MON88913) has a broader window of application for glyphosate than MON1445 event found in DP 555BG/RR.

FM 1740B2F is 9 days earlier than DP 555BG/RR; FM 1740B2F first fruiting branch measures significantly lower than DP 555BG/RR: FM 1740B2F sets fruit one node lower than DP 555BG/RR; FM 1740B2F is significantly shorter (plant height) than DP 555BG/RR; FM 1740B2F has a higher seed and lint index than DP 555BG/RR; FM 1740B2F has a lower lint percentage than DP 555BG/RR; FM 1740B2F sets a lower number of seeds per boll than DP 555BG/RR. However, FM 1740B2F seed weighs more (grams seed per boll) than DP 555BG/RR; FM 1740B2F has less locules per boll than DP 555BG/RR; FM 1740B2F has a larger boll (based on a 25 boll sample) than DP 555BG/RR; FM 1740B2F has a longer fiber length and stronger fiber than DP 555BG/RR; FM 1740B2F has a more uniform and higher elongated fiber than DP 555BG/RR.

Example 2

An Essentially Derived Variety of FM 1740B2F

A variety has been essentially derived from FM 1740B2F by the process of the transgression of the Event LLCotton 25, USDA-APHIS petition 02-042-01p, U.S. Pat. No. 6,818,807, into plants of the variety FM 1740B2F via the method of recurrent backcrossing and selecting the plants which express the characteristics of FM 1740B2F combined with the resistance to the herbicide glyfosinate.

Example 3

An Essentially Derived Variety of FM 1740B2F

A variety has been essentially derived from FM 1740B2F by the process of the transgression of the Event LLCotton 25 via genetic engineering in regenerable cells or tissue of FM 1740B2F and the subsequent selection of regenerated plants, which express the characteristics of FM 1740B2F combined with the resistance to the herbicide gluphosinate.

Example 4

An Essentially Derived Variety of FM 1740B2F

A variety has been essentially derived from FM 1740B2F by the selection of an induced or natural occurring mutant plant or off-type plant from plants of FM 1740B2F, which plant retains the expression of the phenotypic characteristics of FM 1740B2F and differs only from FM 1740B2F in the expression of one, two, three, four, or five of the characteristics listed in Table 1, when grown side by side with FM 1740B2F on one or two locations in one or two growing seasons.

Deposit Information

Applicant has deposited 2500 seeds of cotton variety FM 1740B2F disclosed herein with the American Type Culture Collection (ATCC), 10801 University Boulevard, Manassas, Va 20110, USA, under ATCC Accession No. PTA-12372. The seeds were deposited with the ATCC on Jan. 5, 2012, under the Budapest Treaty. Access to this deposit will be available during the pendency of the application to the Commissioner of Patents and Trademarks and persons determined by the Commissioner to be entitled thereto upon request. The deposit will be maintained for a period of 30 years, or 5 years after the most recent request, or for the enforceable life of the patent, whichever is longer, and will be replaced if it becomes nonviable during that period. Applicant does not waive any rights granted under this patent or under the Plant Variety Protection Act (7 U.S.C. 2321 et seq.).

TABLE 1

| Description of Characteristic | Possible Expression/Note | Variety FM 1740B2F | Variety DP555BG\RR |
|---|---|---|---|
| General Plant Type | | | |
| Plant Habit | spreading, intermediate, compact | Compact | Spreading |
| Foliage | sparse, intermediate, dense | Intermediate | Intermediate |
| Stem Lodging | lodging, intermediate, erect | Erect | Erect |
| Fruiting Branch | clustered, short, normal | Short | Normal |
| Growth | determinate, intermediate, indeterminate | Intermediate | Indeterminate |
| Leaf color | greenish yellow, light green, medium green, dark green | Medium Green | Medium Green |
| Boll Shape | Length < Width, L = W, L > W | Length > Width | Length > Width |
| Boll Breadth | broadest at base, broadest at middle | Middle | Middle |
| Maturity | date of 50% open bolls | Sept. 17 | Sept. 26 |
| Plant | | | |
| cm. to first Fruiting Branch | from cotyledonary node | 17.4 | 27.3 |
| No. of nodes to 1st Fruiting Branch | excluding cotyledonary node | 6.3 | 7.8 |
| Mature Plant Height in cm. | cotyledonary node to terminal | 106.9 | 138.8 |
| Leaf: upper most, fully expanded leaf | | | |
| Type | normal, sub-okra, okra, super-okra | Normal | Normal |
| Pubescense | absent, sparse, medium, dense | Medium | Sparse |
| Nectaries | present, absent | Present | Present |
| Stem Pubescense | glabrous, intermediate, hairy | Intermediate | Intermediate |
| Glands (Gossypol) | absent, sparse, normal, more than normal | | |
| Leaf | | Normal | Normal |
| Stem | | Normal | Normal |
| Calyx lobe | (normal is absent) | Absent/Normal | Absent/Normal |
| Flower | | | |
| Petals | cream, yellow | Cream | Cream |
| Pollen | cream, yellow | Cream | Cream |
| Petal Spot | present, absent | Absent | Absent |
| Seed | | | |
| Seed Index | g/100 seed fuzzy basis | 8.7 | 6.3 |
| Lint Index | g lint/100 seeds | 6.6 | 4.8 |
| Boll | | | |
| Lint percent, picked | | 41.4 | 42.7 |
| Gin Turnout, stripped | | | |
| Number of Seeds per Boll | | 33.7 | 37.2 |
| Grams Seed Cotton per Boll | | 2.95 | 2.35 |
| Number of Locules per Boll | | 4.36 | 4.7 |
| Boll Type | storm proof, storm resistant, open | Open | Open |
| Fiber Properties | | | |
| Method HVI | | | |
| Length, inches, 2.5% SL | | 1.16 | 1.12 |
| Uniformity (%) | | 85.5 | 83.3 |
| Strength, T1 (g/tex) | | 31.6 | 30.3 |
| Elongation, E1 (%) | | 8.4 | 7.9 |
| Micronaire | | 5.1 | 5 |
| Diseases, Insects and Pests | | | |
| Bacterial Blight race 1 | susceptible = S, moderately susceptible = MS | | |
| Bacterial Blight race 2 | moderately resistant = MR, resistant = R | | |
| Bacterial Blight Race 18 | | | |
| Verticillium Wilt | | | |
| Bollworm | | | |
| Cotton Leafworm | | | |
| Fall Armyworm | | | |
| Pink Bollworm | | | |
| Tobacco Budworm | | | |

TABLE 2

PLANT MEASUREMENT ANALYSIS INTERNAL TRIAL - LELAND, MS 2007

| ENTRY_NAME | BOLL_LEN (mm) | BOLL_WID (mm) | CMFB (cm) | NFB (cm) | HT (cm) | FB1 (cm) | PED (mm) | LOCKS_BOLL (number) | ST_LEN (mm) |
|---|---|---|---|---|---|---|---|---|---|
| FM 1740B2F | 1.88 | 1.37 | 18.03 | 6.27 | 111.70 | 11.16 | 2.00 | 4.57 | 0.23 |
| DP 555BG/RR | 1.63 | 1.17 | 27.62 | 7.90 | 140.80 | 11.96 | 2.81 | 4.70 | 0.31 |

TABLE 2-continued

PLANT MEASUREMENT ANALYSIS INTERNAL TRIAL - LELAND, MS 2007

| ENTRY_NAME | BOLL_LEN (mm) | BOLL_WID (mm) | CMFB (cm) | NFB (cm) | HT (cm) | FB1 (cm) | PED (mm) | LOCKS_BOLL (number) | ST_LEN (mm) |
|---|---|---|---|---|---|---|---|---|---|
| GRAND MEAN | 1.84 | 1.32 | 20.72 | 7.01 | 116.71 | 10.95 | 2.53 | 4.48 | 0.30 |
| C.V., % | 2.08 | 2.44 | 10.49 | 5.96 | 5.13 | 8.65 | 8.95 | 3.58 | 18.32 |
| LSD (0.05) | 0.06 | 0.05 | 3.65 | 0.70 | 10.04 | 1.59 | 0.38 | 0.27 | 0.09 |

TABLE 3

PLANT MEASUREMENT ANALYSIS INTERNAL TRIAL - AZLIN, MS 2007

| ENTRY_NAME | BOLL_LEN (mm) | BOLL_WID (mm) | CMFB (cm) | NFB (cm) | HT (cm) | FB1 (cm) | PED (mm) | LOCKS_BOLL (number) | ST_LEN (mm) |
|---|---|---|---|---|---|---|---|---|---|
| FM 1740B2F | 1.82 | 1.32 | 16.93 | 6.30 | 102.10 | 10.56 | 2.18 | 4.67 | 0.20 |
| DP 555BG/RR | 1.58 | 1.26 | 27.02 | 8.03 | 136.90 | 12.02 | 2.81 | 4.63 | 0.22 |
| GRAND MEAN | 1.82 | 1.32 | 20.44 | 7.15 | 112.16 | 10.96 | 2.54 | 4.51 | 0.26 |
| C.V., % | 1.99 | 2.69 | 10.39 | 5.38 | 4.71 | 12.99 | 7.58 | 4.94 | 17.49 |
| LSD (0.05) | 0.06 | 0.06 | 3.56 | 0.65 | 8.87 | 2.39 | 0.32 | 0.37 | 0.08 |

TABLE 4

YIELD AND FIBER TRAITS FROM TRIAL-LELAND, MS 2007

| Entry Name | Lint % | LBS LINT/ACRE | Length (in) | Len. Unif (%) | Strength (g/tex) | Elongation (%) | Micronaire |
|---|---|---|---|---|---|---|---|
| FM 1740B2F | 40.76 | 1220 | 1.17 | 85.9 | 31.1 | 8.7 | 5.0 |
| DP 555BG/RR | 42.09 | 1042 | 1.12 | 83.1 | 30.6 | 8.1 | 5.0 |
| Mean | 37.89 | 1027 | 1.15 | 84.7 | 32.0 | 8.0 | 5.0 |
| C.V., % | 2.23 | 8 | 1.88 | 0.8 | 4.8 | 2.9 | 3.6 |
| LSD (0.05) | 1.83 | 134 | 0.05 | 1.4 | 3.3 | 0.5 | 0.4 |

TABLE 5

YIELD AND FIBER TRAITS FROM TRIAL-AZLIN, MS 2007

| Entry Name | Lint % | LBS LINT/ACRE | Length (in) | Len. Unif (%) | Strength (g/tex) | Elongation (%) | Micronaire |
|---|---|---|---|---|---|---|---|
| FM 1740B2F | 42.04 | 1561 | 1.15 | 85.1 | 32.1 | 8.2 | 5.3 |
| DP 555BG/RR | 43.22 | 1170 | 1.12 | 83.6 | 29.9 | 7.8 | 5.0 |
| Mean | 39.16 | 1246 | 1.14 | 84.6 | 31.4 | 8.1 | 5.0 |
| C.V., % | 2.18 | 11 | 2.77 | 0.9 | 5.7 | 2.9 | 3.1 |
| LSD (0.05) | 1.85 | 229 | 0.07 | 1.7 | 3.9 | 0.5 | 0.3 |

TABLE 6

2007 TRANSGENIC COMMERCIAL VARIETY TRIAL - BOLLGARD/HERBICIDE TOLERANT - BCSI DRS (MS DELTA) FIBER DATA ACROSS ALL LOCATIONS

| | | MEAN HVI FIBER QUALITY | | | | |
|---|---|---|---|---|---|---|
| ENTRY NAME | BOLL SIZE (g) | LEN (in) | UNIF (%) | STREN (g/tex) | ELONG (%) | MIC |
| FM 1740B2F | 4.8 | 1.18 | 84.2 | 32.6 | 9.8 | 5.3 |
| DP 555BG/RR | 4.3 | 1.13 | 81.7 | 30.9 | 9.8 | 5.0 |
| GRAND MEAN | 4.9 | 1.18 | 84.0 | 32.3 | 9.7 | 4.9 |
| C.V., % | 6.7 | 2.7 | 1.3 | 4.2 | 8.1 | 3.2 |

CITED REFERENCES

Lawrence P. Burdett, "Cotton Variety 02T15," U.S. Pub. No. 20090049564.

F. N. Briggs, and P. F Knowles, 1967: "Introduction to Plant Breeding", Rheinhold Publishing Corporation.

H. F. Sakhanoko et al 2004: "Induction of Somatic embryogenesis and Plant Regeneration in Select Georgia and Pee Dee Cotton Lines", Crop Science 44: 2199-2205.

Umbecke et al 1988: "Genetic engineering of cotton plants and lines", Patent application number EP0290355.

Reynaerts et al 2000: "Improved method for *Agrobacterium* mediated transformation of cotton", Patent application number WO 0071733.

P. Stam, 2003: "Marker-assisted introgression: speed at any cost?" Proceedings of the Eucarpia Meeting on Leafy Vegetable Genetics and Breeding, Noordwijkerhout, The Netherlands, 19-21 Mar. 2003. Eds. Th. J. L. van Hintum, A. Lebeda, D. Pink, J. W. Schut. P117-124.

Trolinder et al. "Herbicide tolerant cotton plants having event EE-GH1." U.S. Pat. No. 6,818,807 (2004).

What is claimed is:

1. A seed of cotton variety FM 1740B2F, wherein a representative sample of seed of said variety was deposited under ATCC Accession No. PTA-12373.

2. A plant of cotton variety FM 1740B2F, or a part thereof, wherein a sample of seed of said variety was deposited under ATCC Accession No. PTA-12373.

3. A regenerable plant part of the plant of claim 2.

4. The plant part of claim 3, wherein said plant part is pollen, an ovule or a cell.

5. A tissue culture of regenerable cells of the plant of claim 2.

6. The tissue culture of claim 5, wherein the regenerable cells are from embryos, meristematic cells, pollen, leaves, roots, root tips, anther, pistil, flower, seed, or stem.

7. A cotton plant regenerated from the tissue culture of claim 5, wherein the regenerated cotton plant expresses all of the physiological and morphological characteristics of cotton variety FM 1740B2F, a representative sample of seed of said variety having been deposited under ATCC Accession No. PTA-12373.

8. A method of producing cotton seed, comprising crossing the plant of claim 2 with itself or a second cotton plant.

9. The method of claim 8, wherein said method is a method of preparing hybrid cotton seed, and said method comprises crossing a plant produced by growing the seed of cotton variety FM 1740B2F, wherein a representative sample of seed of said variety was deposited under ATCC Accession No. PTA-12373, with a second, distinct cotton plant.

10. An F1 hybrid cotton seed produced by the method of claim 9.

11. An F1 hybrid cotton plant produced by growing the seed of claim 10.

12. A method of producing a cotton plant having an added desired trait, wherein the method comprises introducing a transgene conferring the desired trait into the cotton plant of claim 2.

13. The method of claim 12, wherein the desired trait is selected from the group consisting of male sterility, herbicide tolerance, insect or pest resistance, disease resistance, modified fatty acid metabolism, modified carbohydrate metabolism and modified cotton fiber characteristics.

14. The method of claim 13, wherein the desired trait is herbicide tolerance and the tolerance is conferred to an herbicide selected from the group consisting of glyphosate, sulfonylurea, imidazolinone, dicamba, glufosinate, phenoxy proprionic acid, cyclohexanedione, triazine, benzonitrile, and bromoxynil.

15. The method of claim 12, wherein the desired trait is insect resistance and the transgene encodes a *Bacillus thuringiensis* (Bt) endotoxin.

16. A cotton plant produced by the method of claim 12, wherein the plant comprises the desired trait and all of the physiological and morphological characteristics of cotton variety FM 1740B2F when grown in the same environmental conditions.

17. A method of introducing a single locus conversion into cotton variety FM 1740B2F comprising:
(a) crossing a plant of variety FM 1740B2F, a representative sample of seed of said variety having been deposited under ATCC Accession No. PTA-12373, with a second plant comprising a desired single locus to produce F1 progeny plants;
(b) selecting F1 progeny plants that have the single locus to produce selected F1 progeny plants;
(c) crossing the selected progeny plants with at least a first plant of variety FM 1740B2F to produce backcross progeny plants;
(d) selecting backcross progeny plants that have the single locus and physiological and morphological characteristics of cotton variety FM 1740B2F to produce selected backcross progeny plants; and
(e) repeating steps (c) and (d) one or more times in succession to produce selected second or higher backcross progeny plants that comprise the single locus and all of the physiological and morphological characteristics of cotton variety FM 1740B2F when grown in the same environmental conditions.

18. The method of claim 17, wherein the single locus confers a trait selected from the group consisting of male sterility, herbicide tolerance, insect or pest resistance, disease resistance, modified fatty acid metabolism, modified carbohydrate metabolism, and modified cotton fiber characteristics.

19. The method of claim 18, wherein the trait is tolerance to an herbicide selected from the group consisting of glyphosate, sulfonylurea, imidazolinone, dicamba, glufosinate, phenoxy proprionic acid, cyclohexanedione, triazine, benzonitrile, and bromoxynil.

20. The method of claim 18, wherein the trait is insect resistance and the insect resistance is conferred by a transgene encoding a *Bacillus thuringiensis* endotoxin.

21. A cotton plant produced by the method of claim 17, wherein the plant has the desired single locus and all of the physiological and morphological characteristics of cotton variety FM 1740B2F.

22. A method of producing an inbred cotton plant derived from the cotton variety FM 1740B2F, the method comprising the steps of
(a) preparing a progeny plant derived from cotton variety FM 1740B2F, a representative sample of seed of said variety having been deposited under ATCC Accession No. PTA-12373, by crossing cotton variety FM 1740B2F with a cotton plant of a second variety;
(b) crossing the progeny plant with itself or a second plant to produce a seed of a progeny plant of a subsequent generation;
(c) growing a progeny plant of a subsequent generation from said seed and crossing the progeny plant of a subsequent generation with itself or a second plant; and
(d) repeating steps (b) and (c) for an additional 3-10 generations with sufficient inbreeding to produce an inbred cotton plant derived from the cotton variety FM 1740B2F.

23. A method of producing a commodity plant product comprising obtaining the plant of claim 2, or a part thereof, and producing said commodity plant product therefrom.

24. The method of claim 23, wherein the commodity plant product is lint or cotton seed oil.

25. A protoplast produced from the tissue culture of claim 5.

26. A method of producing a cotton plant having an added desired trait comprising introducing a transgene conferring the desired trait into the plant of claim 7.

27. A cotton plant produced by the method of claim 26, wherein the plant comprises the desired trait and all of the physiological and morphological characteristics of cotton variety FM 1740B2F when grown in the same environmental conditions.

* * * * *